United States Patent [19]
Melcher et al.

[11] Patent Number: 5,915,746
[45] Date of Patent: Jun. 29, 1999

[54] SWAB AND METHOD OF MANUFACTURING AND USING IT

[75] Inventors: Jerald R. Melcher, Omaha; Debra A. Speichert, Bellevue, both of Nebr.

[73] Assignee: Nagl Manufacturing Co., Omaha, Nebr.

[21] Appl. No.: 08/273,466

[22] Filed: Jul. 11, 1994

Related U.S. Application Data

[62] Division of application No. 08/000,205, Jan. 4, 1993, Pat. No. 5,358,480, which is a division of application No. 07/823,366, Jan. 21, 1992, Pat. No. 5,212,847.

[51] Int. Cl.[6] .......................... A47L 13/46; A61M 35/00
[52] U.S. Cl. .......................... 29/450; 15/244.1; 15/209.1; 604/1; 604/2
[58] Field of Search ................ 29/450; 15/244.1, 15/209.1; 604/1, 2, 3, 4

[56] References Cited

U.S. PATENT DOCUMENTS

| | | | |
|---|---|---|---|
| 2,510,490 | 9/1950 | Ager | 128/269 |
| 3,058,139 | 10/1962 | Dryden | 15/244 |
| 3,134,124 | 5/1964 | Horn | 15/244 |
| 3,262,459 | 7/1966 | Sheehan | 132/9 |
| 4,609,301 | 9/1986 | Benarrouch | 401/196 |
| 4,856,136 | 8/1989 | Janssen | 15/244.3 |

*Primary Examiner*—Larry I. Schwartz
*Assistant Examiner*—Marc W. Butler
*Attorney, Agent, or Firm*—Vincent L. Carney

[57] ABSTRACT

To provide an autoclavable swab, a fibrous applicator pad is formed with a narrow slit and a handle with a plurality of barb means extending away from its longitudinal axis and from a first end toward a second end. The opening is sufficient in size to receive the first end of the handle and the adjacent portion through at least 25 percent of the applicator pad, whereby the barbs, once inserted, engage the applicator pad material within the opening to resist removal of the handle.

5 Claims, 3 Drawing Sheets

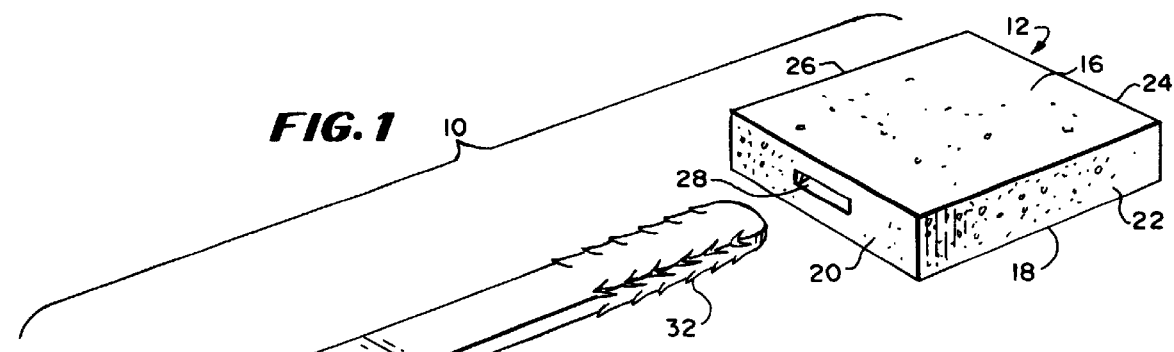
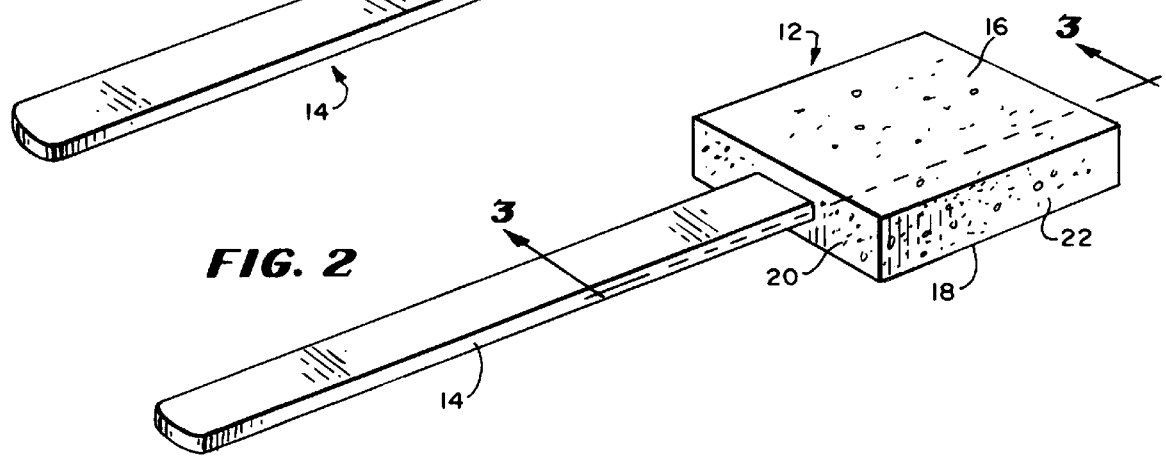
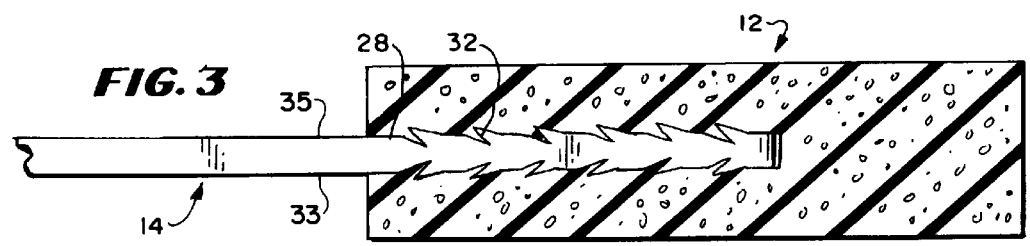
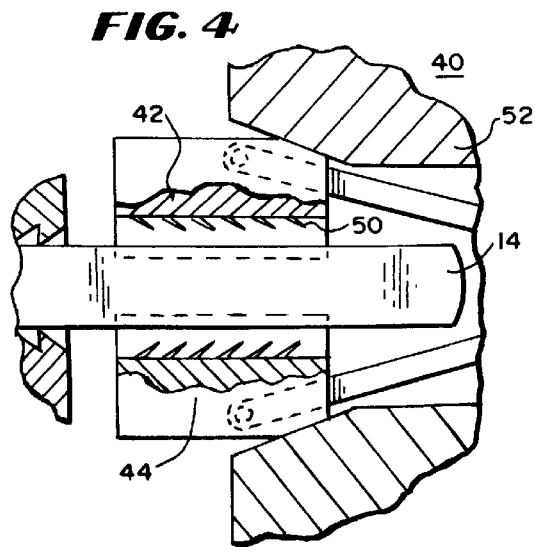
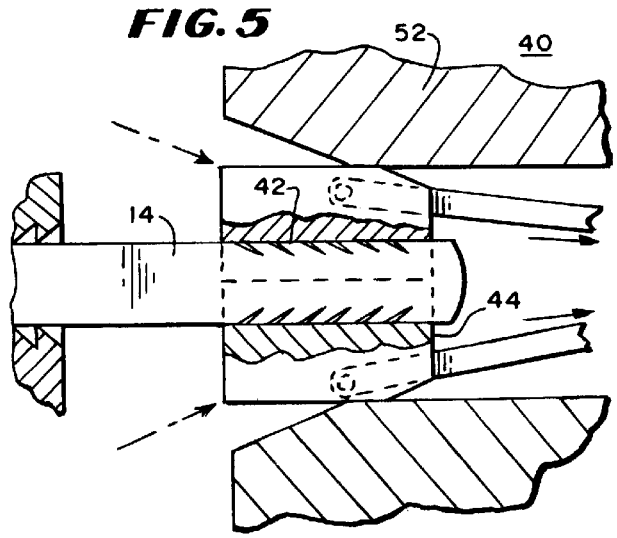

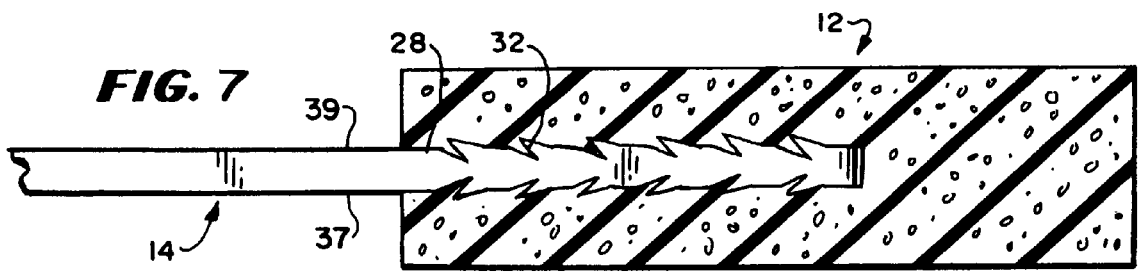

5,915,746

SWAB AND METHOD OF MANUFACTURING AND USING IT

REFERENCE TO RELATED APPLICATIONS

This application is a division of application Ser. No. 08/000,205 filed Jan. 4, 1993 now U.S. Pat. No. 5,358,480, which is a division of application Ser. No. 07/823,366 for SWAB AND METHOD OF MANUFACTURING AND USING IT filed by Jerry R. Melcher et al. on Jan. 21, 1992, and assigned to the same assignee as this application, now U.S. Pat. No. 5,212,847.

BACKGROUND OF THE INVENTION

This invention relates to swabs, which may be used to apply medication or make-up or the like or to clean and/or dry surfaces.

One class of applicator includes a handle and an absorbant pad fastened to the handle. This type of applicator is used for applying, spreading and removing many types of substances such as medication, eye make-up for the eyelid, cleaning liquids and the like. In the prior art applicators, the swabs are generally glued to a rigid handle.

The prior art applicators have several disadvantages under some circumstances, such as: (1) they are relatively expensive to assemble; (2) they are not as durable as desirable for some applications; (3) the glue, when it is used, does not withstand autoclaving or withstand solvents and cleaning for some sterile applications; and (4) the welding process is relatively expensive.

SUMMARY OF THE INVENTION

Accordingly, it is an object of the invention to provide a novel swab.

It is a further object of the invention to provide a novel method for assembling handles to absorbant pads.

It is a still further object of the invention to provide a novel swab which can resist autoclaving and solvents and is relatively durable.

It is a further object of the invention to provide a swab having a rigid handle with barb-like members that engage portions of an absorbant pad to be rigidly fastened in place.

In accordance with the above and further objects of the invention, a swab includes a rigid holder, sufficiently long to be conveniently held in one hand, and an absorbant pad capable of being used to sweep across a surface to either wipe the surface or apply material to it. The swab may be of any material capable of retaining substances on its surface but preferably is an absorbant sponge-like pad having an opening in one side extending into it at least twenty-five percent of the distance to the end of the pad.

The holder is a rigid member having a first end and a second end with the first end being adapted to extend into the opening in the pad and the second end being intended to be held by the user. The first end is adapted to extend into the opening in the pad by having barbs or prongs extending outwardly from the longitudinal axis and rearwardly to the second end so that it may be inserted into said opening and catch on the fabric therein with a portion extending outwardly to the second end to provide a handle. The barbs on the holder can be formed by cutting slots with a die in its outer surface or can be molded.

There should be at least four barbs with at least two being cut into the periphery of the holder near the first end in spaced apart relation from each other but in a common plane at an angle to the longitudinal axis to provide support on either side. The handle should extend into the pad at least 25 percent of the distance from one side of the pad to the other in the direction of the insertion of the handle and may extend all the way through the handle although in the preferred embodiment it extends 90 percent of the distance into the pad.

The barbs must be sufficiently long to form a firm grip within the pad and should be for that purpose at least 3 percent of the distance through the handle in a direction perpendicular to the longitudinal axis but should extend at an angle to the longitudinal axis to form barbs that extend outwardly and rearwardly capable of catching within the pad.

From the above description, it can be understood that the swab of this invention has several advantages such as: (1) it is easily fabricated and easily assembled since the fabrication of the pad may be molded with a slot size the same size as the handle formed in it or it may be cut or burned and the handle may be a simple member which is die cut or molded; (2) it can be made of autoclavable material and will withstand autoclaving since it does not require any adhesive that might deteriorate; and (3) it has been found to be exceptionally durable in use.

SUMMARY OF THE DRAWINGS

The above-noted and other features of the invention will be better understood from the following detailed description when considered with reference to the accompanying drawings, in which:

FIG. 1 is an exploded, perspective view of a swab in accordance with the invention;

FIG. 2 is a perspective drawing of a swab in accordance with the invention; and

FIG. 3 is a sectional view taken through lines 3—3 of the swab of FIG. 2;

FIGS. 4 and 5 are simplified sectional views of an apparatus for forming barbs on a holder;

FIG. 7 is a sectional view showing of the swab shown in FIG. 3 taken from the opposite side of the holder as that shown in FIG. 3.

DETAILED DESCRIPTION

Figure 6:
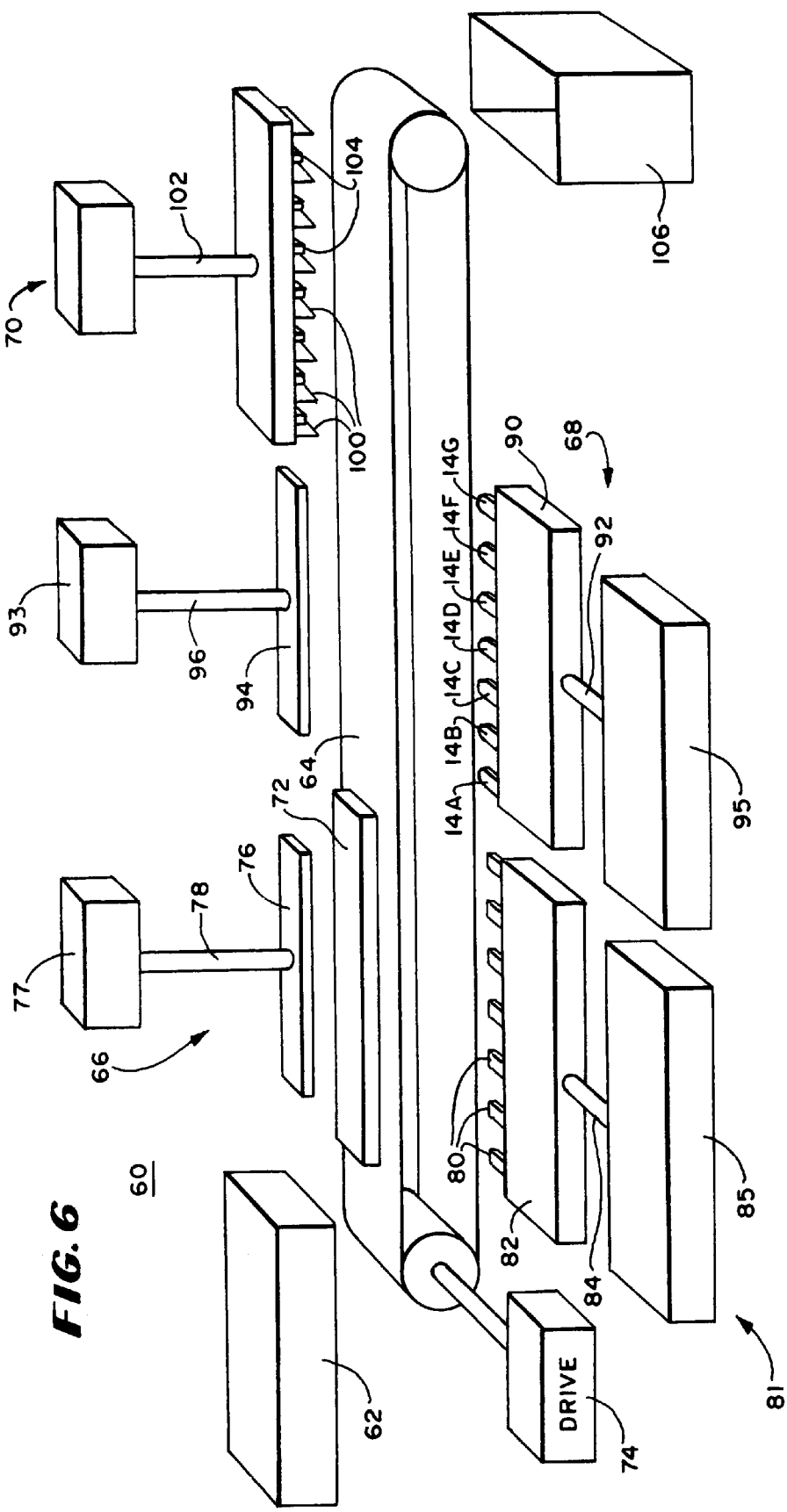
FIG. 6 is a diagramatic view of a high speed system for making the swab of FIG. 1.

In FIG. 1, there is shown an exploded perspective view of a swab or applicator 10 having an absorbant pad section 12, and a handle 14. The pad section 12, in the preferred embodiment, is a substantial right, regular parallelopiped having relatively wide, flat, parallel, opposite surfaces 16 and 18 connected by four side walls 20, 22, 24 and 26, each substantially perpendicular to the wider surfaces 16 and 18. However, the pad may be of any other shape suitable for the use to which the swab is to be put such as substantially cylindrical or ellipsoidal or spherical or the like.

In the preferred embodiment, the right regular parallelopiped-shaped pad section 12 has dimensions of two inches by two inches by three-quarters of an inch and is formed of an open cell plastic such as foam polyurethane. In one side, such as in the side 20, there is an opening 28 one-half inch long and one-thirty-second of an inch high extending two inches into the pad for receiving the handle 14. The opening 28 conforms to the outer shape of the handle 14 with a tight fit so that the barbs engage the surface when the handle 14 is inserted and resists removal. When the handle is not inserted, the sides of the opening may be touching in the preferred embodiment and the opening may be a slit cut into the pad by a thin bladed knife or formed during foaming or burned with a hot wire and cutting of the pad.

The handle 14 is a rigid, elongated member having a length sufficient to extend into the pad 12 with a gripping relationship, sized for an interference fit with the opening such as 28 and extending outwardly a sufficient distance to be easily gripped, which for some applications need only be one-half of an inch, but for other applications that require more vigorous action, the handle 14 should extend several inches.

For square cross-section handles, the portion entering the pad thickness should be at least 1/16th inch. Flat handles should have at least a 1/64th inch thickness with a 1/8th inch width. The length of each type of handle should be at least one inch long. Other shapes, such as triangular, may be used provided there is a corner in the portion entering the pad. A cylindrical handle can be used with a flatened portion entering the pad.

In the preferred embodiment, the handle 14 is substantially a right, regular parallelopiped having dimensions of six inches by five-eighths of an inch by one-eighth of an inch having 36 row cuts on its first end, formed as herringbone 32. The cuts are backwardly-shaped and outwardly extending barbs with each row including at least four barbs, each in a different one of the four corners or edges (33, 35, 37 and 39) of the handle 14 (shown in FIGS. 3 and 7). The barbs are chevron-shaped with the point of the chevron pointing inwardly at an angle to the longitudinal axis of the opening in the pad and the longitudinal axis of the handle and toward the pad and the legs of the chevron pointing outwardly at an angle to the same longitudinal axis and in the direction of the other end of the handle to engage the pad at an angle.

The number of barbs and the size of the barbs are selected to provide a sturdy handle and a firm grip against removal of the handle but their specific arrangement is selected for ease in fabrication. The handle may be of other shapes but the portion entering the pad should have at least one corner.

In FIG. 2, there is shown a perspective view of the applicator 10 showing the manner in which the handle 14 is inserted into the pad section 12. As shown in this view, one end of the handle 14 is extended almost fully through the opening 28 and extends straight back through most of the length of the pad section 12 and the number of barbs is generally spread throughout that length to form a firm gripping action sufficient to prevent the handle 14 from being easily removed without tearing of the pad.

In FIG. 3, there is shown a sectional view taken through lines 3—3 of FIG. 2 showing the opening 28 through the open cell polyurethane pad section 12 to form an interference fit with the handle 14 (FIG. 1). This pad is designed for use so that in an application relating to cleaning with methyl ethyl chlorine or other solvents, it may have any one of a variety of widths. For cosmetics, it is used as an eye-lid applicator and is much smaller and less absorbant on its surfaces.

In FIGS. 4 and 5, there are shown simplified sectional views of apparatus 40 for cutting the barbs in a handle 14 comprising first and second die members 42 and 44 respectively. Die member 44 includes a slot with a depth equal to approximately half of the width of the handle 14 and die member 44 includes a slot 48 having a depth approximately half of the width of the handle 14 so that the two dies, when brought together, tightly engage the edges of the handle 14.

The widths of the slots conform to the thickness of the handle 14 and at their bottom ends each of them includes sharply pointed serations 50 adapted to cut the corners of the handle 14. A mechanism 52 is adapted to force the two dies 44 and 46 together at an angle in the direction of the first or forward end of the handle 14 to cut barbs therein as shown in FIG. 5 and a mechanism 54 forces the handle forward.

To form the swab, a plurality of elongated members such as the flat wood strips shaped as a right, regular parallelopiped having dimensions of six inches by five-eighths of an inch by one-eighth of an inch are obtained and assembled for insertion into the apparatus 40. They are fed into the apparatus and the two dies 44 and 46 are brought together to cut into their ends, row cuts formed as a herringbone, pointing backwardly away from the end that is to be inserted in the pad. After the wood members have been cut, they are ejected from the apparatus. In the preferred embodiment, they will be shaped as the handle 14.

The pad portions are formed by molding foam plastic to shape or to a larger shape for cutting into the final shape, either with the slit for receiving the handle or without the slit. If molded without the slit, the slit is cut with a hand operated knife or burned with a hot electrode or by an automatic apparatus that feeds the pads into position and cuts the slits with a movable blade. The pad and handle may be assembled before packaging or packages may be prepared with disassembled pads and handles and the insertion of the handle into the pad may be done by the user. For some applications, the assembly is autoclaved at high temperatures in excess of 200 degrees, and preferably 270 degrees, Fahrenheit and then sealed in a sterile package.

In FIG. 6, there is shown a diagramatic view of equipment 60 for rapidly making swabs including a pad molding station 62, an opening-forming station 66, a conveyor 64, a handle inserting station 68 and a cutting station 70. The conveyor 64 is positioned so that its top run extends between the molding station 62, the opening forming station 66, the handle forming station 68 and the cutting station 70. A hopper to receive swabs is located at the end of the conveyor.

In operation, elongated sections 72 of fibrous pad material are formed in the molding station 62 and transmitted to the conveyor 64 which carries them from station to station in sequence. The elongated sections 72 are several times larger than a swab but have the same height and depth. Each elongated section is held in station 66 while openings are cut or burned into a plurality of locations along the elongated section 72. The drive motor then moves the elongated section 72 to another station 68 where it is held for the application of a plurality of holders. After which it is moved by the drive to another station which cuts individual swabs and permits them to drop off into a hopper for later collection.

The mold station 62 in the preferred embodiment includes a mold that forms the right regular parallelopiped elongated sections 72, each of which has a height and a depth the size of the individual swab but a length the size of a plurality of swabs. In one embodiment, a plurality of parallel openings extending horizontally parallel to the ends and the top and perpendicular to the length of the elongated section 72 are molded, but in the preferred embodiment, a solid right regular parallelopiped is formed and moved onto the conveyor 64 without openings. The conveyor 64 is driven by a drive mechanism 74 which is programmed to move the sections 72 in sequence to stop them at the stations. Thus, the pads are moved by the programmed drive mechanism 74 from station to station such as the stations 66, 68 and 70.

The opening-forming station 66 includes a pad holder 66 and an opening former 81. The pad holder 66 includes a manual or electronically controlled hydraulic actuator 77, a piston 78 and a flat clamp 76. The flat clamp is mounted to the piston above the conveyor 64 for movement by the actuator downwardly against a section 72 to hold it and upwardly to release it. The opening former 81 includes a piston 84, a manual or electronically controlled hydraulic actuator 85, an electrode holder 82 and a plurality of parallel cutting blades or electrically heated wires or plates 80 positioned side-by-side. The cutting blades are the size of the intended openings in the pads and spaced from each other horizontally with their center to center distance being equal to the width of a pad. The holder 82 in which the cutters are mounted is adapted to apply a heating electrical current to the cutters. The holder for the cutters is mounted to the piston 84 for movement by the hydraulic actuator 85 into the section 72 while the section 72 is held by the holder clamp 76. Of course, the holder can be operated manually if desired.

At the opening forming station 66, the section 72 is manually or automatically stopped on the conveyor 64 under the flat clamp 76. The actuator 77 hydraulically moves the top holding clamp 76 by a hydraulically-operated piston 78 to clamp the top of the section 72. While it is held, the plurality of opening formers 80 connected to holders 82 are moved by the second piston 84 into the section 72. The opening formers 80 in the preferred embodiment are electrically heated and burn openings of the proper size into the section 72, but may instead be blades to cut the openings as slits.

After the openings are made, the holder 82 is withdrawn by the piston 84 and the clamp 76 is withdrawn by the piston 78. The drive 74 then moves the section 72 to the handle inserting station 68 for the insertion of handles. The handle inserting station 68 includes a clamping mechanism 93 similar in construction to the clamping mechanism at station 66 and a movable handle holding section 90 driven by a piston 92 under the control of an actuator 95 in the same manner as the holder 82 in the opening forming station 66.

At the station 68, handles which have been cut such as by mechanisms disclosed in FIGS. 4 and 5 or handles which have been molded with corner barbs are held in a holder 90 adapted to be driven by a hydraulically-operated piston 92. The clamp 94 is adapted to hold the sections 72 in place by a piston 96. With the sections 72 held in place, the piston 92 moves the handles into the sections 72 and withdraws leaving the handles in place. The clamp 94 is then lifted and the drive 74 moves the pad on the conveyor belt 64 to the station 70. New handles are manually or automatically fed into position.

At the station 70, a plurality of cutting knives or electrodes extending parallel to the ends of the sections 72 shown at 100 are moved downwardly by a piston 102 to cut the sections 72 into a plurality of swabs, each of which includes a different one of the handles. The cutters are then moved upwardly while the sections 72 are held down by spring-biased fingers 104 interleaved between the cutting edges. When the spring-biased fingers 104 have been lifted, the conveyor 64 moves the cut swabs so that they drop into a hopper 106 for later collection.

In use, the pads and handles are assembed by inserting the barbed end of the handles into corresponding ones of the pads if this has not already been done. The combination may be autoclaved, if desired. The pad is then coated with the desired material and spread over the surface or in a wiping application the dry pad is moved over the surface to remove substances.

From the above description, it can be understood that the swab of this invention has several advantages, such as: (1) it is easily fabricated and easily assembled since the fabrication of the pad may be molded with a slot size the same size as the handle formed in it and the handle may be a simple member which is die cut; (2) it can be made of autoclavable material and will withstand autoclaving since it does not require any adhesive that might deteriorate; and (3) it has been found to be exceptionally durable in use.

Although a preferred embodiment of the invention has been described with some particularity, many modifications and variations in the preferred embodiment are possible in light of the above teachings. Therefore, it is to be understood that, within the scope of the appended claims, the invention may be practiced other than as specifically described.

What is claimed is:

1. A method of frabricating a plurality of handles each adapted to have a corresponding one handle end inserted in a corresponding one pad end of a plurality of pads including the steps of:

forming a plurality of strips shaped as right, regular parallelopipes having dimensions of at least one inch by one-eighth of an inch by one-thirty-second of an inch from an autoclavable material;

forming barbs on the one handle end of each of said strips whereby said handles are formed with barbs on each of said one handle ends;

wherein each of said one handle end of said plurality of said handles has four corners and at least four barbs are formed in each of the four corners of each handle.

2. A method of fabricating a plurality of handles in accordance with claim 1 wherein the step of forming barbs includes a step of making a plurality of cuts in at least one row, each cut being formed as herringbone, pointing backwardly away from said handle end that is adapted to be inserted in an opening in said pad.

3. A method of fabricating a plurality of handles in accordance with claim 1 wherein the step of forming barbs on one end of said strip includes a step of forming at least four barbs with at least two of said four barbs being cut into a periphery of the strip near the one end in spaced apart relation from each other but in a common plane at an angle to a longitudinal axis of the strip to provide support within the pad on either side of the strip.

4. A method of fabricating a plurality of handles in accordance with claim 3 wherein the step of forming barbs includes cutting slits into said handle sufficiently long to provide a firm grip within the pad wherein the slits extend a first distance equal to at least 3 percent of a second distance through the handle; said second distance being the distance through the handle in a direction perpendicular to the longitudinal axis; said first distance extending at an angle to the longitudinal axis to form barbs that extend outwardly and rearwardly whereby they are capable of catching within the pad to prevent removal of the handle from the pad without tearing the pad.

5. A method of fabricating a plurality of handles in accordance with claim 1 wherein the step of forming a plurality of strips includes the step of forming a plurality of strips each having a uniform cross-section along its length.

* * * * *